(12) United States Patent
Urushiyama et al.

(10) Patent No.: US 8,932,488 B2
(45) Date of Patent: Jan. 13, 2015

(54) THERMOLUMINESCENT PHOSPHOR AND METHOD OF PRODUCING THE SAME

(75) Inventors: Akio Urushiyama, Toshima-ku (JP); Yuji Tomizawa, Saitama (JP)

(73) Assignee: Rikkyo Gakuin, Tokyo (JP)

( * ) Notice: Subject to any disclaimer, the term of this patent is extended or adjusted under 35 U.S.C. 154(b) by 108 days.

(21) Appl. No.: 13/820,614

(22) PCT Filed: Sep. 2, 2011

(86) PCT No.: PCT/JP2011/070045
§ 371 (c)(1),
(2), (4) Date: Mar. 4, 2013

(87) PCT Pub. No.: WO2012/029951
PCT Pub. Date: Mar. 8, 2012

(65) Prior Publication Data
US 2013/0161560 A1 Jun. 27, 2013

(30) Foreign Application Priority Data
Sep. 3, 2010 (JP) ................. 2010-197876

(51) Int. Cl.
| | | |
|---|---|---|
| C09K 11/63 | (2006.01) | |
| C09K 11/08 | (2006.01) | |
| G01T 1/02 | (2006.01) | |
| C09K 11/58 | (2006.01) | |
| C09K 11/55 | (2006.01) | |
| G01T 1/11 | (2006.01) | |
| A61N 5/10 | (2006.01) | |

(52) U.S. Cl.
CPC ............ *C09K 11/63* (2013.01); *C09K 11/58* (2013.01); *C09K 11/0877* (2013.01); *C09K 11/55* (2013.01); *C09K 11/634* (2013.01); *G01T 1/11* (2013.01); *A61N 5/1071* (2013.01)
USPC ................................... 252/301.4 R

(58) Field of Classification Search
CPC ..... C09K 11/58; C09K 11/55; C09K 11/0877
USPC ................................... 252/301.4 R
See application file for complete search history.

(56) References Cited

U.S. PATENT DOCUMENTS

| | | |
|---|---|---|
| 4,248,731 A | 2/1981 | Takenaga et al. |
| 4,290,909 A | 9/1981 | Takenaga et al. |
| 2003/0062486 A1 | 4/2003 | Shimizu et al. |

FOREIGN PATENT DOCUMENTS

| | | |
|---|---|---|
| GB | 2 027 735 A | 2/1980 |
| JP | 2003-183637 | 7/2003 |

(Continued)

OTHER PUBLICATIONS

Holovey et al, "Luminescent Properties of Glassy and Crystallized $(Li_2B_4O_7+ xB_2O_3)0.999(CuO)0.001$ (x=0-16.67 mol%) Materials", Inorganic Materials, 2006, vol. 42, No. 11, pp. 1265-1272.*

(Continued)

*Primary Examiner* — Carol M Koslow
(74) *Attorney, Agent, or Firm* — Nixon & Vanderhye P.C.

(57) ABSTRACT

There is provided a thermoluminescent phosphor characterized in that a distribution of the emission intensity of thermoluminescence is present in a visible range that does not overlap the peak of the heating-caused emission intensity of the thermoluminescent phosphor itself and also has one peak within a temperature range in which a resin to be used as a binder can resist heat optically. There is also provided a method of producing the thermoluminescent phosphor. More specifically, there are provided a thermoluminescent phosphor that comprises lithium heptaborate as a base material and copper as a luminescent center present in the base material and which is characterized in that the distribution of the emission intensity of thermoluminescence versus temperature is a sole and monomodal distribution within the range of from 45° C. to 130° C., and a method of producing the thermoluminescent phosphor.

10 Claims, 11 Drawing Sheets

(56) References Cited

FOREIGN PATENT DOCUMENTS

| JP | 2007-183149 | 7/2007 |
| JP | 2010-127930 | 6/2010 |
| JP | 2011-52179 A | 3/2011 |

OTHER PUBLICATIONS

CDPS-ICDD Card No. 32-549.

International Search Report for PCT/JP2011/070045 mailed Dec. 6, 2011.

Extended European Search Report in EP 11 82 1965 issued Mar. 19, 2014.

Jiang Aidong et al, "Structure of Lithium Heptaborate, $Li_3B_7O_{12}$", Acta Cryst. (1990). C46, 1999-2001.

Narita et al, "Dosimetric Verification in Intensity Modulated Radiation Therapy," Journal of the Japanese Society of Radiological Technology, vol. 58, No. 6, Jun. 2002, pp. 761-772; and an excerpted translation.

Ozdemir et al, "Investigation of thermoluminescence properties of metal oxide doped lithium triborate," J. Mater. Sci. (2007) 42: 8501-8508.

\* cited by examiner (A)

(B)

(A)

(B)

(A)

(B)

THERMOLUMINESCENT PHOSPHOR AND METHOD OF PRODUCING THE SAME

This application is the U.S. national phase of International Application No. PCT/JP2011/070045 filed 2 Sep. 2011 which designated the U.S. and claims priority to JP 2010-197876 filed 3 Sep. 2010, the entire contents of each of which are hereby incorporated by reference.

TECHNICAL FIELD

This invention relates to a thermoluminescent phosphor and a method of producing the thermoluminescent phosphor, and in particular, to a thermoluminescent phosphor usable as a material for a dosimeter for acquiring the three-dimensional dose distribution of radiation and which is tissue equivalent to the human body, and to a method of producing the thermoluminescent phosphor.

BACKGROUND ART

As is well known, in recent radiation therapy, attention has been centered on advanced stereotactic radiation therapies such as three-dimensional conformal radiation therapy (3D-CRT) and intensity modulated radiation therapy (IMRT), which are intended to deliver radiation such as hard X-rays, electron beams, or accelerated particle beams while appropriately setting the shape and dose level of the radiation to be delivered (see, for example, Non-patent Document 1). In these therapies, various parameters such as irradiation site, coverage, and output are set using, for example, a therapy planning apparatus, before delivering radiation. By this means, the effort of, for example, delivering a high dose of radiation to only a lesion while avoiding organs-at-risk neighboring the lesion, has been made to accomplish precise treatment. Hence, in these radiation therapies, it is important to set the above various parameters to appropriate values. Other required matters are a high level of mechanical precision of an irradiator apparatus itself and a high level of precision in the control of various filters, line width enlargement devices and the like with which the irradiator apparatus is equipped.

Hence, in implementation of the above radiation therapies, it is necessary to verify the settings of various parameter values and the precision by measuring the doses of radiation to be used in the therapies. Particularly, as to the stereoscopic dose distribution of radiation near a lesion to be irradiated with the radiation, much empirical data are required to be obtained.

A thermoluminescent layered product formed by layering a plurality of thermoluminescent plates stereoscopically is well known as a dosimeter for measuring the stereoscopic dose distribution, i.e., three-dimensional dose distribution, of radiation (see, for example, Patent Document 1).

According to Patent Document 1, the thermoluminescent plate constituting the thermoluminescent layered product is in the shape of a flat plate and formed of, as a material, a thermoluminescent substance, more specifically, a thermoluminescent substance comprising lithium tetraborate or the like as a base material and manganese as a luminescent center added to the base material. By delivering radiation to the thermoluminescent layered product comprising the thermoluminescent plate, the three-dimensional dose distribution of the radiation can be obtained.

More specifically, after being irradiated with radiation, the thermoluminescent layered product is divided into the thermoluminescent plates and then each of the thermoluminescent plates is heated. From the thermoluminescent plates, the light intensity distribution of thermoluminescence caused by this heating is acquired. As is well known, there is a certain relation between the light intensity of thermoluminescence and the radiation dose. Hence, from the information on the light intensity distribution thus acquired, the information on the planar exposure dose distribution (hereinafter, also referred to simply as "dose distribution"), i.e., two-dimensional dose distribution, of radiation along a surface irradiated with the radiation can be obtained. The thus obtained information on each dose distribution is reconstructed as information on the dose distribution of the radiation delivered to the original thermoluminescent layered product, whereby a stereoscopic, i.e., three-dimensional dose distribution can be acquired.

Further, according to Patent Document 1, the thermoluminescent plate constituting the thermoluminescent layered product is adjusted to be tissue equivalent to living tissues constituting the human body (e.g., muscle tissue), that is, to be equivalent in effective atomic number to such living tissues.

Hence, in the thermoluminescent layered product described in Patent Document 1, when irradiated with radiation, effects such as photoelectric interaction, Compton effect, and electron pair producing effect are produced at the same level as those in the human body. Thus, when such a thermoluminescent layered product is used as a dosimeter, data on the dose of radiation delivered to the human body can be acquired directly from measured values without making various corrections.

In addition to the manganese-containing lithium tetraborate ($Li_2B_4O_7$) disclosed in Patent Document 1 referred to above, for example, the thermoluminescent substances described below which can be used as materials for a dosimeter are well known (see, for example, Non-patent Documents 2, 3, and 4).

That is, Non-patent Documents 2 and 3 each disclose that copper-containing lithium triborate ($LiB_3O_5$) is a thermoluminescent substance exhibiting thermoluminescence.

Non-patent Document 4 discloses that a thermoluminescent substance can be obtained as a composition produced by thermal reaction of lithium tetraborate, boron oxide, and copper(II) oxide. Non-patent Document 4 also discloses that thermoluminescent substances having various properties are formed according to the mixing ratios of these materials, i.e., lithium tetraborate, boron oxide, and copper(II) oxide by varying the ratios.

To prepare a dosimeter for measuring three-dimensional dose distribution by using the thermoluminescent substance of Non-patent Document 2, 3, or 4 as a material for the dosimeter, first, a resin is used as a binder to mold the thermoluminescent substance into a product in the shape of a flat plate, as disclosed, for example, in Patent Document 2. A plurality of the plates are then layered in the same manner as in the case of the thermoluminescent plate disclosed in Patent Document 1 described above, whereby it is deemed that a thermoluminescent layered product can be prepared.

CITATION LIST

Patent Documents

Patent Document 1: JP 2010-127930 A
Patent Document 2: JP S61-269100 A

Non-Patent Documents

Non-patent Document 1: The Journal of the Japanese Society of Radiological Technology, Vol. 58, No. 6, "Dosimetric Verification in Intensity Modulated Radiation Therapy", June 2002, pp. 761-772

Non-patent Document 2: Zeynep Ozdemir Jemir, Gulhan Ozbayoglu, and Aysen Yilmaz, J. Mater Sci (2007) 42: 8501-8508

Non-patent Document 3: CDPS ICDD Card No. 32-549

Non-patent Document 4: V. W. Holovey, V. I. Lyamayev, A. M. Solomon, N. N. Birov, P. P. Puga, and V. T. Maslyuk, Neorganicheskie Materialy (Inorganic Materials), 2006, Vol. 42, No. 11, pp. 1384-1392: Inorganic Materials, 2006, Vol. 42, No. 11, pp. 1265-1272

SUMMARY OF INVENTION

Technical Problem

In the cases of the thermoluminescent plate and thermoluminescent layered product which comprise the manganese-containing lithium tetraborate disclosed in Patent Document 1, the emission intensity distribution of thermoluminescence is present in the wavelength range of from 550 nm to 750 nm.

In general, when a substance having thermoluminescent properties is heated to a high temperature, the substance itself emits light as a result of this heating, as is well known. If this substance is manganese-containing lithium tetraborate, a shorter wavelength envelope of the emission is present in a wavelength range close to 600 nm in the intensity distribution of the heating-caused light emission of the manganese-containing lithium tetraborate itself. Thus, the wavelength range of the heating-caused emission intensity distribution and the wavelength range of the emission intensity distribution of thermoluminescence overlap.

Further, the thermoluminescent plate and thermoluminescent layered product of Patent Document 1 need to be heated to a temperature at which the heating-caused light emission described above can occur, in order to produce thermoluminescence.

Hence, for accurate measurement of the emission intensity of thermoluminescence, it is necessary to separate thermoluminescence emission and heating-caused light emission, by using, for example, a near-infrared cut filter.

The copper-containing lithium triborate described in Non-patent Document 2 or 3 has the problem of the low emission intensity of thermoluminescence.

In the case of a thermoluminescent substance described in Non-patent Document 4, the distribution of the emission intensity of thermoluminescence versus wavelength is present in the ultraviolet range.

As already described, to prepare a dosimeter for measuring three-dimensional dose distribution by using the thermoluminescent substance described in Non-patent Document 4, it is necessary to use a resin as a binder to mold the thermoluminescent substance into a plate. In particular, to prepare a dosimeter that is tissue equivalent to the human body, it is preferred to form a plate using as a binder a resin that is equivalent in effective atomic number to the human body, specifically, for example, an epoxy resin. More specifically, a well-known epoxy resin that is equivalent in effective atomic number to the human body and thus preferred when used as a binder is, for example, GM-9005 produced by Blenny Giken Corporation.

However, such an epoxy resin used as a binder has the property of absorbing ultraviolet light. Hence, if the thermoluminescent substance described in Non-patent Document 4 is used as a material for a dosimeter intended for measuring three-dimensional dose distribution, the problem is that the thermoluminescence is absorbed by the resin, resulting in decreased emission intensity of thermoluminescence.

In addition to the foregoing thermoluminescent substance characterized in that a distribution of the emission intensity of thermoluminescence is present in the ultraviolet range, Non-patent Document 4 discloses a thermoluminescent substance characterized in that a distribution of the emission intensity of thermoluminescence is present in a wavelength range close to 410 nm (hereinafter, also referred to as the second thermoluminescent substance of Non-patent Document 4).

In the case of the second thermoluminescent substance of Non-patent Document 4, a distribution of the emission intensity of thermoluminescence versus temperature is present in each of the low temperature region, i.e., the temperature range of from about 94° C. to about 124° C. and the high temperature region, i.e., the temperature range of from about 172° C. to about 186° C.

The presence of a plurality of distributions of the emission intensity of thermoluminescence versus temperature means that a plurality of metastable states in which a thermoluminescent substance, when irradiated with radiation, accumulates energy exist at different temperatures. When such a thermoluminescent substance is heated for observation of thermoluminescence, energy is transferred between the metastable states. As a result, energy accumulated in the thermoluminescent substance in a certain metastable state is involved in different distributions of the emission intensity of thermoluminescence in a plurality of temperature regions. Thus, the relation between the exposure dose and the emission intensity of thermoluminescence becomes complex, and consequently, various corrections need to be made when calculating the exposure dose from measured emission intensity of thermoluminescence.

Further, if a thermoluminescent substance characterized in that a plurality of such distributions of the emission intensity of thermoluminescence versus temperature are present is used repeatedly as a dosimeter, the thermoluminescent substance needs to be heated to at least a temperature higher than the temperature range in the high temperature region in which a distribution of the emission intensity of thermoluminescence is present, before performing a subsequent measurement in order to release the energy accumulated by irradiation with radiation in a preceding measurement.

However, the epoxy resin described above, more specifically, for example, GM-9005, does not have optical heat resistance at a temperature of 180° C. or higher. That is, GM-9005 discolors by being heated to 180° C. or higher. Hence, GM-9005 absorbs light emitted in thermoluminescence at a temperature of 180° C. or higher. For this reason, if a dosimeter intended for measuring three-dimensional dose distribution is prepared using the second thermoluminescent substance of Non-patent Document 4 as a material, the problem is that the distribution of the emission intensity of thermoluminescence in the high temperature region cannot be measured at sufficient emission intensity.

As a result of intensive and extensive studies, the present inventors have found that a thermoluminescent phosphor comprising copper-containing lithium heptaborate ($Li_3B_7O_{12}$) as a thermoluminescent substance exhibits a distribution of the high emission intensity of thermoluminescence in a wavelength range that is not only a visible range but also a range of wavelengths shorter than 600 nm, and that the emission intensity distribution is present alone within a temperature range in which resins can resist heat.

The present inventors also have found that a thermoluminescent phosphor comprising copper-containing lithium heptaborate can be formed by adjusting the mixing ratio of lithium tetraborate, boron oxide, and copper(II) oxide as materials and the temperature for heat treatment of a mixture of these materials.

This invention has been accomplished to solve the conventional problems described above.

Thus, the first object of this invention is to provide a thermoluminescent phosphor that can be used as a material for a dosimeter intended for measuring three-dimensional dose distribution and which is characterized in that a distribution of the emission intensity of thermoluminescence versus wavelength is present in a visible range that does not overlap the above heating-caused emission intensity distribution and that the emission intensity of thermoluminescence is high compared with that of the above copper-containing lithium triborate, and is also to provide a method of producing the thermoluminescent phosphor.

The second object of this invention is to provide a thermoluminescent phosphor that achieves the first object described above and which is characterized in that a sole and monomodal distribution of the emission intensity of thermoluminescence versus temperature is present in a temperature range in which a resin to be used as a binder is optically resistant, that is, the resin does not discolor, and is also to provide a method of producing the thermoluminescent phosphor.

The third object of this invention is to provide a thermoluminescent phosphor that achieves the first and second objects described above and which exhibits high emission intensity, with an effective atomic number showing that the thermoluminescent phosphor is tissue equivalent to the human body, and is also to provide a method of producing the thermoluminescent phosphor.

Solution to Problem

To achieve the objects described above, the thermoluminescent phosphor according to this invention has the following features.

More specifically, the thermoluminescent phosphor according to this invention comprises lithium heptaborate as a base material and copper as a luminescent center present in this base material, and the distribution of the emission intensity of thermoluminescence versus wavelength is a sole and monomodal distribution and is present in a visible range of wavelengths shorter than 600 nm.

Further, in the thermoluminescent phosphor according to this invention, the distribution of the emission intensity of thermoluminescence versus temperature is preferably a sole and monomodal distribution in the range of from 45° C. to 130° C.

The method of producing a thermoluminescent phosphor according to this invention includes the following first and second steps.

More specifically, in the first step, lithium tetraborate, boron oxide, and copper(II) oxide are mixed together to form a mixture.

In this first step, lithium tetraborate and boron oxide are mixed in the molar ratio of 3:1.

Next, in the second step, the mixture is subjected to thermal treatment to change the mixture into a thermoluminescent phosphor comprising lithium heptaborate as a base material and copper as a luminescent center present in the base material.

The method of producing a thermoluminescent phosphor according to this invention also includes the following first and second steps.

More specifically, in the first step, lithium tetraborate, boron oxide, and copper(II) oxide are mixed together to form a mixture.

In this first step, lithium tetraborate and boron oxide are mixed in the molar ratio of 6:1.

Next, in the second step, the mixture is subjected to thermal treatment to change the mixture into a thermoluminescent phosphor comprising lithium heptaborate as a base material and copper as a luminescent center present in the base material.

The method of producing a thermoluminescent phosphor according to this invention further includes the following first and second steps.

More specifically, in the first step, lithium tetraborate, boron oxide, and copper(II) oxide are mixed together to form a mixture.

In this first step, lithium tetraborate and boron oxide are mixed in the molar ratio of 2:1.

Next, in the second step, the mixture is subjected to thermal treatment to change the mixture into a thermoluminescent phosphor comprising lithium heptaborate as a base material and copper as a luminescent center present in the base material.

Further, in the method of producing a thermoluminescent phosphor according to this invention, it is preferred to adjust the weights of lithium tetraborate, boron oxide, and copper (II) oxide and mix them together in the first step to thereby adjust the effective atomic number of the thermoluminescent phosphor to be formed.

Advantageous Effects of Invention

The thermoluminescent phosphor according to this invention comprises lithium heptaborate as a base material, whereby the distribution of the emission intensity of thermoluminescence versus wavelength is present in a visible range of wavelengths shorter than 600 nm. Hence, as for the thermoluminescence of the thermoluminescent phosphor according to this invention, the heating-caused light emission described above does not have to be considered, and thus, a near-infrared cut filter, for example, is not required to be used.

Further, the thermoluminescent phosphor according to this invention can be formed such that a sole and monomodal distribution of the emission intensity of thermoluminescence versus temperature is present in the temperature range of from 40° C. to 130° C. In this case, the distribution of the emission intensity of thermoluminescence is present in the temperature range in which, for example, the foregoing epoxy resin that is equivalent in effective atomic number to the human body can resist heat optically, that is, the resin does not discolor.

As a result, to prepare a dosimeter for measuring three-dimensional dose distribution, the epoxy resin described above, more specifically, for example, GM-9005, can be used as a binder to form a plate.

Hence, the thermoluminescent phosphor according to this invention can be used as a material that is used for a dosimeter for measuring three-dimensional dose distribution and which is tissue equivalent to the human body.

Further, in the thermoluminescent phosphor according to this invention, the distribution of the emission intensity of thermoluminescence is a sole and monomodal distribution, and thus, the relation between the exposure dose and the emission intensity of thermoluminescence is simple, compared with a thermoluminescent phosphor characterized in that a plurality of distributions of the emission intensity of thermoluminescence are present. As a result, complex corrections are not required to be made when calculating the exposure dose from measured emission intensity of thermoluminescence.

The thermoluminescent phosphor according to this invention is formed using lithium heptaborate as a base material, whereby high-intensity thermoluminescence is exhibited as compared with the case of using lithium tetraborate or lithium triborate as a base material.

In the method of producing a thermoluminescent phosphor according to this invention, lithium tetraborate and boron oxide are mixed in the molar ratio of 3:1, 6:1, or 2:1 in the first step, as described above.

As a result, lithium heptaborate serving as a base material can be contained in the thermoluminescent phosphor to be produced.

Moreover, in the method of producing a thermoluminescent phosphor according to this invention, the weights of the foregoing lithium tetraborate, boron oxide, and copper(II) oxide are adjusted when mixing them together, and this process can produce a thermoluminescent plate and thermoluminescent layered product that are tissue equivalent to the human body, that is, equivalent in effective atomic number to the human body.

DESCRIPTION OF EMBODIMENTS

Figure 1:
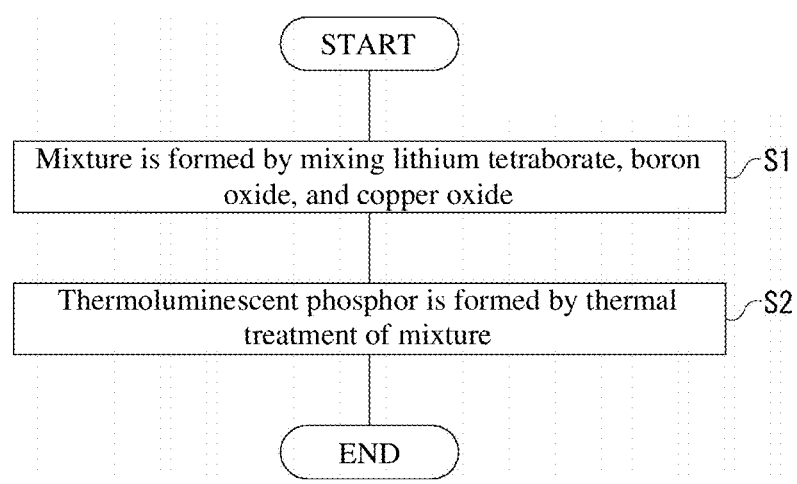
FIG. 1 is a flowchart showing a method of producing a thermoluminescent phosphor according to the first embodiment.

Preferred embodiments of this invention are described below with reference to the drawings. It should be noted that each figure merely shows this invention schematically to the extent that the invention can be understood. Further, the embodiments described below are merely preferred examples, and thus, the structure of this invention is not limited in any way to structural examples described below and illustrated in the drawings. It is clear that the structure of this invention may be altered or modified in many points within the scope of this invention.

First Embodiment

In the first embodiment, thermoluminescent phosphors comprising copper-containing lithium heptaborate as a thermoluminescent substance and methods of producing the thermoluminescent phosphors are described. These production methods include the first and second steps. Each of the steps is described below, starting with the first step.

FIG. 1 is presented to describe the first embodiment of this invention and is a flowchart showing a method of producing a thermoluminescent phosphor according to the first embodiment.

First, in the first step, lithium tetraborate ($Li_2B_4O_7$), boron oxide ($B_2O_3$), and copper(II) oxide (CuO) are ground and mixed to form a mixture (S1).

In this first embodiment, lithium heptaborate serving as a base material of the thermoluminescent phosphor is formed from lithium tetraborate and boron oxide among the foregoing materials for the mixture.

In order to use lithium tetraborate and boron oxide as materials to form lithium heptaborate in good yield, that is, reducing the content of impurities, lithium tetraborate and boron oxide are preferably mixed, for example, in the molar ratio of 3:1, 6:1, or 2:1. More preferably, lithium tetraborate and boron oxide are mixed in the molar ratio of 3:1, whereby lithium heptaborate can be formed in good yield as compared with the case of mixing them in the other molar ratios.

Table 1 shows the amounts of lithium tetraborate and boron oxide that are to be added in each of the preferred examples of the lithium tetraborate to boron oxide molar ratio. It is to be noted that Table 1 also shows the following matters each of which will be described later: preferred examples of the amount of copper(II) oxide to be added in the case of applying each molar ratio; and the effective atomic number applied when producing a thermoluminescent phosphor in the case of applying each molar ratio.

TABLE 1

| $Li_2B_4O_7:B_2O_3$ molar ratio | 3:1 | 6:1 | 2:1 |
| --- | --- | --- | --- |
| Amount of $Li_2B_4O_7$ added (g) | 507.3 g | 1014.6 g | 338.2 g |
| Amount of $B_2O_3$ added (g) | 69.6 g | 69.6 g | 69.6 g |
| Amount of CuO added (g) | 0.58-2.02 g | 1.08-3.79 g | 0.41-1.42 g |
| Effective Atomic No. (0.10 wt % CuO added) | 7.32 | 7.32 | 7.33 |
| Effective Atomic No. (0.35 wt % CuO added) | 7.59 | 7.59 | 7.60 |

To mix lithium tetraborate and boron oxide in the molar ratio of 3:1, it is preferred to mix, for example, 507.3 g of lithium tetraborate and 69.6 g of boron oxide.

To mix lithium tetraborate and boron oxide in the molar ratio of 6:1, it is preferred to mix, for example, 1014.6 g of lithium tetraborate and 69.6 g of boron oxide.

To mix lithium tetraborate and boron oxide in the molar ratio of 2:1, it is preferred to mix, for example, 338.2 g of lithium tetraborate and 69.6 g of boron oxide.

Copper contained in the copper(II) oxide acts as a luminescent center present in the base material of a thermoluminescent phosphor to be produced.

In the thermoluminescent phosphor to be produced in this first embodiment, the emission intensity of thermoluminescence varies according to the amount of copper(II) oxide to be added in this first step.

For this reason, in order to increase the emission intensity of thermoluminescence, it is preferred that copper(II) oxide is incorporated in the mixture (i.e., the mixture of this copper(II) oxide with lithium tetraborate and boron oxide) such that the copper(II) oxide concentration is, for example, within the range of from 0.10 wt % to 0.35 wt %.

Hence, for example, if 507.3 g of lithium tetraborate and 69.6 g of boron oxide are added as described above to form a mixture, copper(II) oxide is preferably incorporated, for example, in a weight within the range of from 0.58 g to 2.02 g.

If 1014.6 g of lithium tetraborate and 69.6 g of boron oxide are added, copper(II) oxide is preferably incorporated, for example, in a weight within the range of from 1.08 g to 3.79 g.

If 338.2 g of lithium tetraborate and 69.6 g of boron oxide are added, copper(II) oxide is preferably incorporated, for example, in a weight within the range of from 0.41 g to 1.42 g.

Next, in the second step, the above mixture prepared in the first step is subjected to thermal treatment to form lithium heptraborate from the lithium tetraborate and boron oxide that are contained in this mixture. As a result, the mixture is changed into a thermoluminescent phosphor comprising lithium heptaborate as a base material and copper as a luminescent center present in the base material (S2).

The temperature for this thermal treatment may be a temperature that allows lithium heptaborate to be generated from this mixture, and the thermal treatment is preferably performed, for example, at a temperature within the range of from 800° C. to 850° C., more preferably at the temperature of 850° C., for about 6 hours. The lithium heptaborate obtained here contains copper as a luminescent center.

As a result, a powdered thermoluminescent substance, that is, a thermoluminescent phosphor which comprises lithium heptaborate serving as a base material formed from lithium tetraborate and boron oxide and copper(II) oxide-derived copper serving as a luminescent center present in the base material can be obtained.

It is to be noted that the copper serving as a luminescent center can be contained, for example, not only as copper as a simple body but also in the state of an oxide or a compound or the like combined with the other substances contained in the thermoluminescent phorphori.

Incidentally, the effective atomic number of muscle tissue of the human body is about 7.42 (see, for example, the Japanese Society of Radiological Technology ed., "*Kaiteiban Hoshasen Keisokugaku*" (Radiation Metrology, revised edition), Iryokagakusha, p. 136 (File No. 1-2)).

Thus, to utilize the thermoluminescent phosphor as a material for a dosimeter used to produce data on the dose of radiation delivered to the human body, the effective atomic number Zeff of the thermoluminescent phosphor is preferably adjusted to a value close to the effective atomic number of the human body. More specifically, in light of methods of calculating effective atomic numbers and the variation occurring when determining the numbers, the effective atomic number of the thermoluminescent plate according to the first embodiment is preferably adjusted to a value within the range of from about 7.3 to about 7.6 or a value close to the range.

In this first embodiment, if 507.3 g of lithium tetraborate, 69.6 g of boron oxide, and copper(II) oxide whose concentration is 0.10 wt % in a mixture to be prepared are mixed together in the first step described above to form the mixture, a thermoluminescent phosphor with an effective atomic number adjusted to about 7.32 can be obtained.

If 507.3 g of lithium tetraborate, 69.6 g of boron oxide, and copper(II) oxide whose concentration is 0.35 wt % in a mixture to be prepared are mixed together in the first step described above to form the mixture, a thermoluminescent phosphor with an effective atomic number adjusted to about 7.59 can be obtained.

Thus, if lithium tetraborate, boron oxide, and copper(II) oxide are mixed together in the first step such that the lithium tetraborate to boron oxide molar ratio is 3:1 and the copper(II) oxide concentration is 0.10 wt % or 0.35 wt % in the mixture, the thermoluminescent phosphor produced according to the first embodiment has an effective atomic number falling within the range of from 7.3 to 7.6, which is preferred as a value close to the effective atomic number of the human body.

Further, as shown in Table 1, if 1014.6 g of lithium tetraborate, 69.6 g of boron oxide, and copper(II) oxide whose concentration is 0.10 wt % in a mixture to be prepared are mixed together in the first step described above to form the mixture, a thermoluminescent phosphor with an effective atomic number adjusted to about 7.32 can be obtained.

If 1014.6 g of lithium tetraborate, 69.6 g of boron oxide, and copper(II) oxide whose concentration is 0.35 wt % in a mixture to be prepared are mixed together in the first step described above to form the mixture, a thermoluminescent phosphor with an effective atomic number adjusted to about 7.59 can be obtained.

If 338.2 g of lithium tetraborate, 69.6 g of boron oxide, and copper(II) oxide whose concentration is 0.10 wt % in a mixture to be prepared are mixed together in the first step described above to form the mixture, a thermoluminescent phosphor with an effective atomic number adjusted to about 7.33 can be obtained.

If 338.2 g of lithium tetraborate, 69.6 g of boron oxide, and copper(II) oxide whose concentration is 0.35 wt % in a mixture to be prepared are mixed together in the first step described above to form the mixture, a thermoluminescent phosphor with an effective atomic number adjusted to about 7.60 can be obtained.

It is to be noted that the effective atomic number $Z_{eff}$ of the thermoluminescent phosphors can be calculated from the formula (I) below, which is shown in, for example, Satoru Fukuda and Masayuki Maekawa, "*Hoshasen Butsurigaku Enshu* (Exercises for Radiation Physics)," Second Edition, pp. 63-64, Toyo Shoten Co., Ltd., 2005.

[Formula 1]

$$Z_{eff} = (a_1 Z_1^{2.94} + a_2 Z_2^{2.94} + a_3 Z_3^{2.94} + \ldots)^{1/2.94} = (\Sigma a_i Z_i^{2.94})^{1/2.94} \qquad (1)$$

In this formula (1), $a_1, a_2, a_3 \ldots$ denote a proportion of electrons that belong to the atomic number $Z_1, Z_2, Z_3 \ldots$ of each atom contained in the compound or mixture, with respect to the total number of electrons.

The present inventors conducted an experiment to determine a preferred value of the molar ratio between lithium tetraborate and boron oxide to be applied in the formation of the mixture in the first step described above and a preferred value of the temperature to be applied in the thermal treatment of the mixture in the second step described above.

Samples prepared in this experiment were a plurality of thermoluminescent phosphors produced using lithium tetraborate and boron oxide in different molar ratios in the first step or a plurality of thermoluminescent phosphors produced by thermal treatment performed at temperatures different from one another in the second step.

The conditions of the preparation of the samples are shown in Table 2.

TABLE 2

| Temp. of Thermal Treatment | $Li_2B_4O_7:B_2O_3$ Molar Ratio | | | | | |
|---|---|---|---|---|---|---|
| | $Li_2B_4O_7$ Only | 6:1 | 3:1 | 2:1 | 1:1 | 1:2 |
| 700° C. | a1 | a2 | a3 | a4 | a5 | a6 |
| 750° C. | b1 | b2 | b3 | b4 | b5 | b6 |
| 800° C. | c1 | c2 | c3 | c4 | c5 | c6 |
| 850° C. | d1 | d2 | d3 | d4 | | |
| 900° C. | e1 | e2 | | | | |

Samples a1, a2, a3, a4, a5, and a6 were prepared by thermal treatment of mixtures at 700° C. in the second step.

Samples b1, b2, b3, b4, b5, and b6 were prepared by thermal treatment of mixtures at 750° C. in the second step.

Samples c1, c2, c3, c4, c5, and c6 were prepared by thermal treatment of mixtures at 800° C. in the second step.

Samples d1, d2, d3, and d4 were prepared by thermal treatment of mixtures at 850° C. in the second step.

Samples e1 and e2 were prepared by thermal treatment of mixtures at 900° C. in the second step.

Samples a1, b1, c1, d1, and e1 were also prepared by mixing only lithium tetraborate and copper(II) oxide to form mixtures, without adding boron oxide, in the first step.

Samples a2, b2, c2, d2, and e2 were also prepared by mixing lithium tetraborate and boron oxide in the molar ratio of 6:1 in the first step.

Samples a3, b3, c3, and d3 were also prepared by mixing lithium tetraborate and boron oxide in the molar ratio of 3:1 in the first step.

Samples a4, b4, c4, and d4 were also prepared by mixing lithium tetraborate and boron oxide in the molar ratio of 2:1 in the first step.

Samples a5, b5, and c5 were also prepared by mixing lithium tetraborate and boron oxide in the molar ratio of 1:1 in the first step.

Samples a6, b6, and c6 were also prepared by mixing lithium tetraborate and boron oxide in the molar ratio of 1:2 in the first step.

It is to be noted that it was confirmed that the following samples could not be obtained as thermoluminescent phosphors because the products were melted in the thermal treatment in the second step: a sample prepared by mixing lithium tetraborate and boron oxide in the molar ratio of 3:1 in the first step and subjecting the resulting mixture to thermal treatment at 900° C. in the second step; a sample prepared by mixing lithium tetraborate and boron oxide in the molar ratio of 2:1 in the first step and subjecting the resulting mixture to thermal treatment at 900° C. in the second step; a sample prepared by mixing lithium tetraborate and boron oxide in the molar ratio of 1:1 in the first step and subjecting the resulting mixture to thermal treatment at 850° C. in the second step; a sample prepared by mixing lithium tetraborate and boron oxide in the molar ratio of 1:1 in the first step and subjecting the resulting mixture to thermal treatment at 900° C. in the second step; a sample prepared by mixing lithium tetraborate and boron oxide in the molar ratio of 1:2 in the first step and subjecting the resulting mixture to thermal treatment at 850° C. in the second step; and a sample prepared by mixing lithium tetraborate and boron oxide in the molar ratio of 1:2 in the first step and subjecting the resulting mixture to thermal treatment at 900° C. in the second step. The other samples were not melted.

Each of these samples obtained was irradiated with 1 Gy of X rays using an irradiator apparatus with an X-ray tube voltage of 6 MV. Subsequently, the each sample was housed in a dark box and exposure with a CCD camera was started, and then the samples were heated to 135° C. in 20 seconds and their emission intensities were observed for 280 seconds while maintaining them at the temperature of 135° C. The X-ray irradiator apparatus used is a SYNERGY linac produced by Elekta.

It is to be noted that, in this experiment, the samples prepared were aligned on one metal plate (e.g. aluminum plate) and the foregoing irradiation with X rays, heating, and observation of the thermoluminescence were performed on the respective samples (collectively) at the same time under identical conditions. Each of the samples was prepared by incorporating the copper(II) oxide in the first step such that the copper(II) oxide concentration of a mixture obtained was 0.35 wt %.

The results of this experiment are described below.

Figure 2:
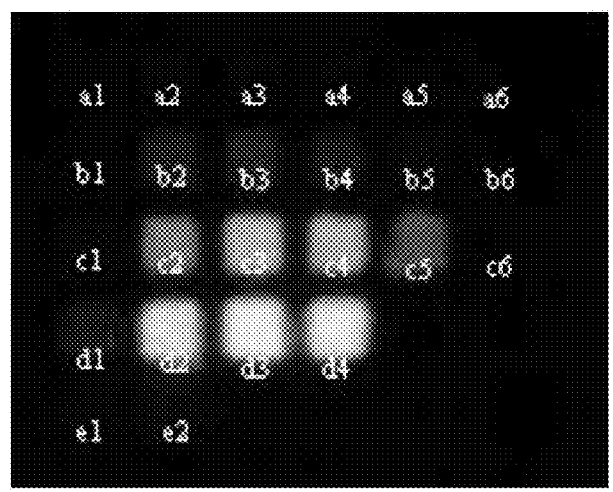
FIGS. 2(A) and 2(B) are presented to compare the emission intensities of thermoluminescence of thermoluminescent phosphors according to the first embodiment.
Figure 2:
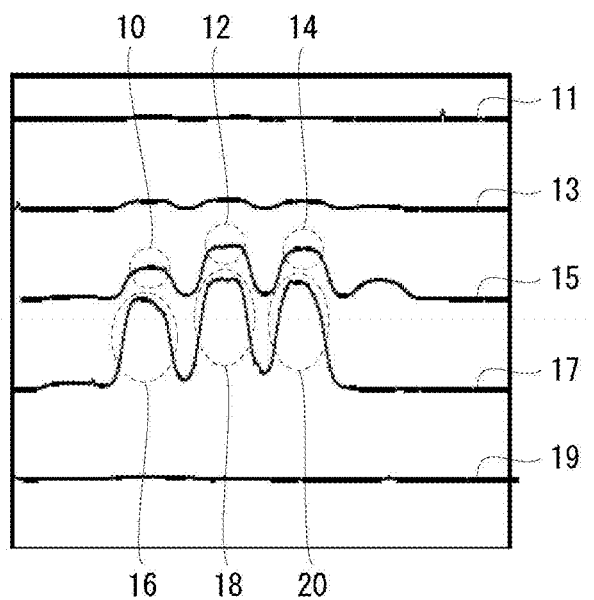

FIGS. 2(A) and 2(B) show the results of this experiment.

FIG. 2(A) is a captured image of light emission caused by thermoluminescence of the samples described above.

It is to be noted that the light emissions marked with symbols a1 to a6, b1 to b6, c1 to c6, d1 to d4, e1, and e2 shown in FIG. 2(A) correspond respectively to the light emissions from Samples a1 to a6, b1 to b6, c1 to c6, d1 to d4, e1, and e2 described above. That is, the alignment of the samples, which were aligned on the metal plate when conducting this experiment, corresponds to the alignment of the symbols shown in FIG. 2(A).

FIG. 2(B) is presented to compare the emission intensities of thermoluminescence of the samples, and the vertical axis shows the relative emission intensities and the horizontal axis corresponds to the positions of the samples each of which is marked with a symbol in FIG. 2(A). More specifically, the intensity distribution line 11 shown in FIG. 2(B) indicates the emission intensity distribution of Samples a1 to a6, the intensity distribution line 13 indicates the emission intensity distribution of Samples b1 to b6, the intensity distribution line 15 indicates the emission intensity distribution of Samples c1 to c6, the intensity distribution line 17 indicates the emission intensity distribution of Samples d1 to d4, and the intensity distribution line 19 indicates the emission intensity distribution of Samples e1 and e2. It is to be noted that these emission intensities were determined by capturing an image of the thermoluminescence with a cooled CCD camera (ATK-314L produced by ATIK Instruments) and then analyzing the image with ImageJ (registered trademark), which is a well-known image-processing software.

The results shown in FIG. 2(A) can clearly confirm that Samples c2, c3, c4, d2, d3, and d4 emitted markedly high-intensity light, as compared with the other samples.

Further, as is clear from each intensity distribution line shown in FIG. 2(B), peak 10 indicating the emission intensity of Sample c2, peak 12 indicating the emission intensity of Sample c3, peak 14 indicating the emission intensity of Sample c4, peak 16 indicating the emission intensity of Sample d2, peak 18 indicating the emission intensity of Sample d3, and peak 20 indicating the emission intensity of Sample d4 exhibit high emission intensities as compared with the cases of the other samples. It can be confirmed from FIG. 2(A) that, in particular, the peak of the emission intensity of Sample d3 exhibits the highest emission intensity.

These results confirmed that, in the first embodiment, the thermoluminescence intensity of a thermoluminescent phosphor to be produced can be increased by mixing lithium tetraborate and boron oxide in the molar ratio of 3:1, 6:1, or 2:1 in the first step and subjecting the resulting mixture to thermal treatment at any temperature within the range of from 800° C. to 850° C. in the second step.

It was confirmed that, in the first embodiment, the highest-intensity thermoluminescence is exhibited, in particular, by a thermoluminescent phosphor to be produced by mixing lithium tetraborate and boron oxide in the molar ratio of 3:1 in the first step and subjecting the resulting mixture to thermal treatment at the temperature of 850° C. in the second step.

Next, the present inventors conducted an experiment on Samples a1, b5, c2, c3, c4, d2, d3, d4, and e2, which were prepared in the experiment related to FIGS. 2(A) and 2(B) described above, in order to identify what substances constituted each of the thermoluminescent phosphors.

In this experiment, Samples a1, b5, c2, c3, c4, d2, d3, d4, and e2 were measured by XRD (X-ray diffraction), whereby the substances contained in these thermoluminescent phosphors were identified based on the spectra obtained. The X-ray diffractometer used is RINT 2000 produced by RIGAKU Corp.

Figure 3:
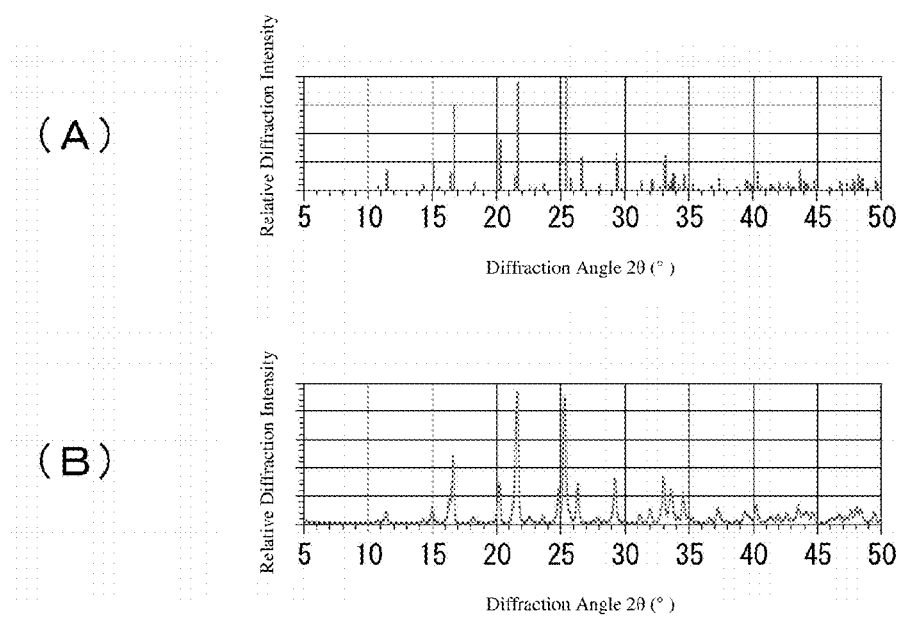
FIGS. 3(A) and 3(B) are presented to identify the components of a thermoluminescent phosphor according to the first embodiment.

FIGS. 3(A) and 3(B) are presented to identify the components of Sample d3, which is a thermoluminescent phosphor described above.

FIG. 3(A) shows an XRD spectrum of Sample d3. FIG. 3(B) shows an XRD spectrum of the lithium heptaborate disclosed in, for example, "J. Aidong, L. Shirong, H. Qingzhen, C. Tianbin, and Acta Crystallogr., Sec. C., 46, 1999 (1990)". Each of these figures shows the relative diffraction intensity on the vertical axis and the diffraction angle (unit: °) on the horizontal axis.

FIGS. 3(A) and 3(B) show that the XRD spectra coincide experimentally in terms of the diffraction angles at which the peaks are present and the relative diffraction intensities of the respective peaks.

This result confirmed that Sample d3 was a thermoluminescent phosphor consisting chiefly of lithium heptaborate.

Figure 4:
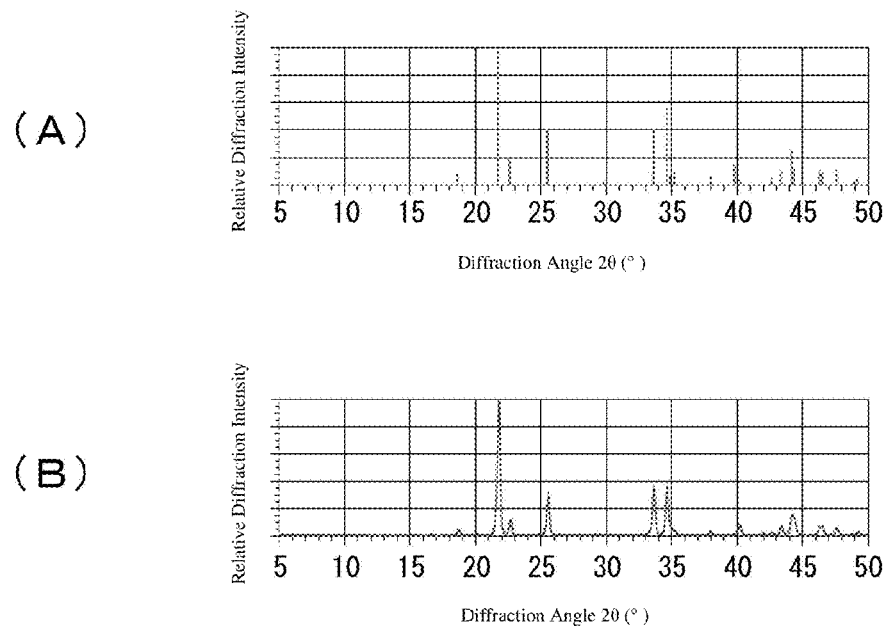
FIGS. 4(A) and 4(B) are presented to identify the components of a thermoluminescent phosphor according to the first embodiment.

FIGS. 4(A) and 4(B) are presented to identify the components of Sample a1, which is a thermoluminescent phosphor described above.

FIG. 4(A) shows an XRD spectrum of Sample a1. FIG. 4(B) shows an XRD spectrum of the lithium tetraborate disclosed in, for example, "JCPDS-ICDD Card No. 18-717". Each of these figures shows the relative diffraction intensity on the vertical axis and the diffraction angle (unit: °) on the horizontal axis.

FIGS. 4(A) and 4(B) show that the XRD spectra coincide experimentally in terms of the diffraction angles at which the peaks are present and the relative diffraction intensities of the respective peaks.

This result confirmed that Sample a1 was a thermoluminescent phosphor consisting chiefly of lithium tetraborate.

Figure 5:
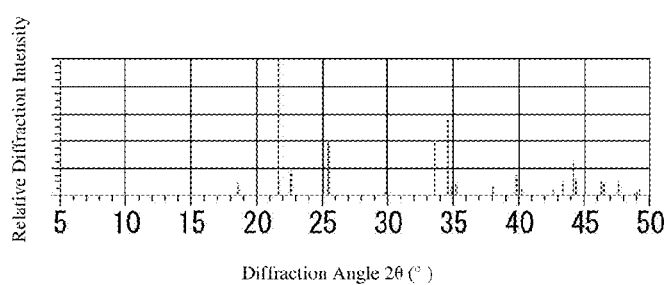
FIGS. 5(A) and 5(B) are presented to identify the components of a thermoluminescent phosphor according to the first embodiment.
Figure 5:
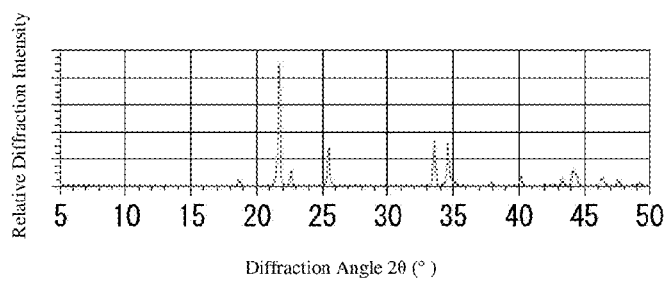

FIGS. 5(A) and 5(B) are presented to identify the components of Sample e2, which is a thermoluminescent phosphor described above.

FIG. 5(A) shows an XRD spectrum of Sample e2. FIG. 5(B) shows an XRD spectrum of the same lithium tetraborate as that shown in FIG. 4(B) described above. Each of these figures shows the relative diffraction intensity on the vertical axis and the diffraction angle (unit: °) on the horizontal axis.

FIGS. 5(A) and 5(B) show that the XRD spectra coincide experimentally in terms of the diffraction angles at which the peaks are present and the relative diffraction intensities of the respective peaks.

This result confirmed that Sample e2 was a thermoluminescent phosphor consisting chiefly of lithium tetraborate.

Figure 6:
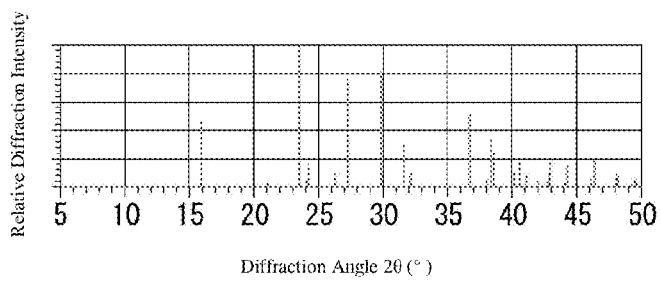
FIGS. 6(A) and 6(B) are presented to identify the components of a thermoluminescent phosphor according to the first embodiment.
Figure 6:
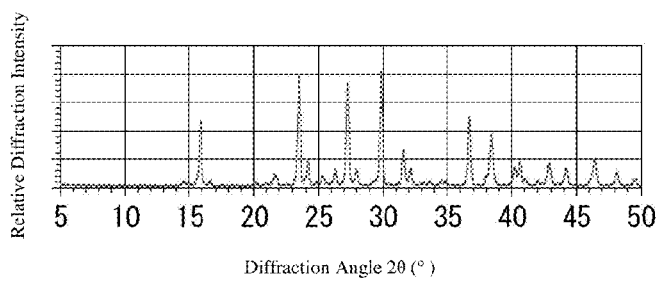

FIGS. 6(A) and 6(B) are presented to identify the components of Sample b5, which is a thermoluminescent phosphor described above.

FIG. 6(A) shows an XRD spectrum of Sample b5. FIG. 6(B) shows an XRD spectrum of the lithium triborate disclosed in, for example, "JCPDS-ICDD Card No. 32-549". Each of these figures shows the relative diffraction intensity on the vertical axis and the diffraction angle (unit: °) on the horizontal axis.

FIGS. 6(A) and 6(B) show that the XRD spectra coincide experimentally in terms of the diffraction angles at which the peaks are present and the relative diffraction intensities of the respective peaks.

This result confirmed that Sample b5 was a thermoluminescent phosphor consisting chiefly of lithium triborate.

Figure 7:
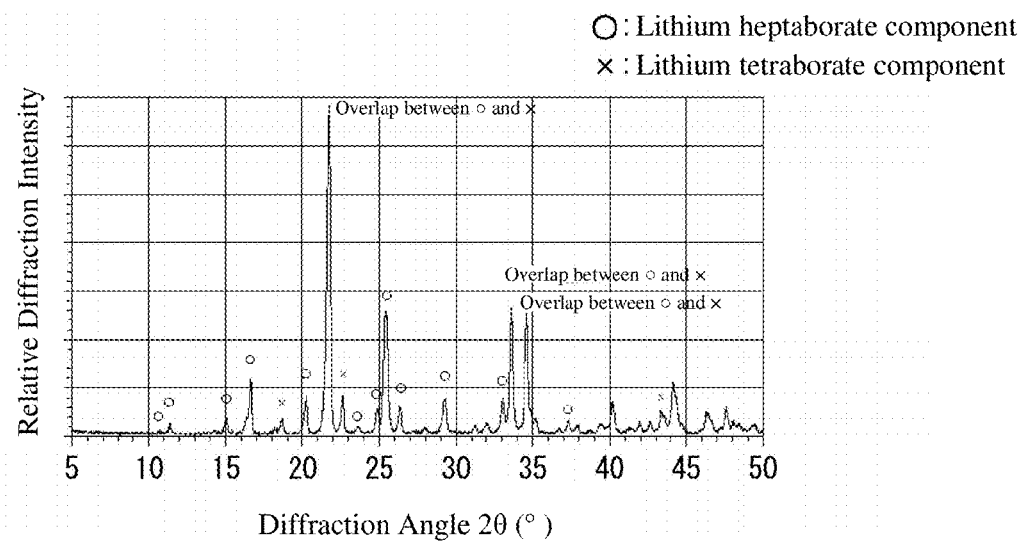
FIG. 7 is presented to identify the components of a thermoluminescent phosphor according to the first embodiment.
Figure 8:
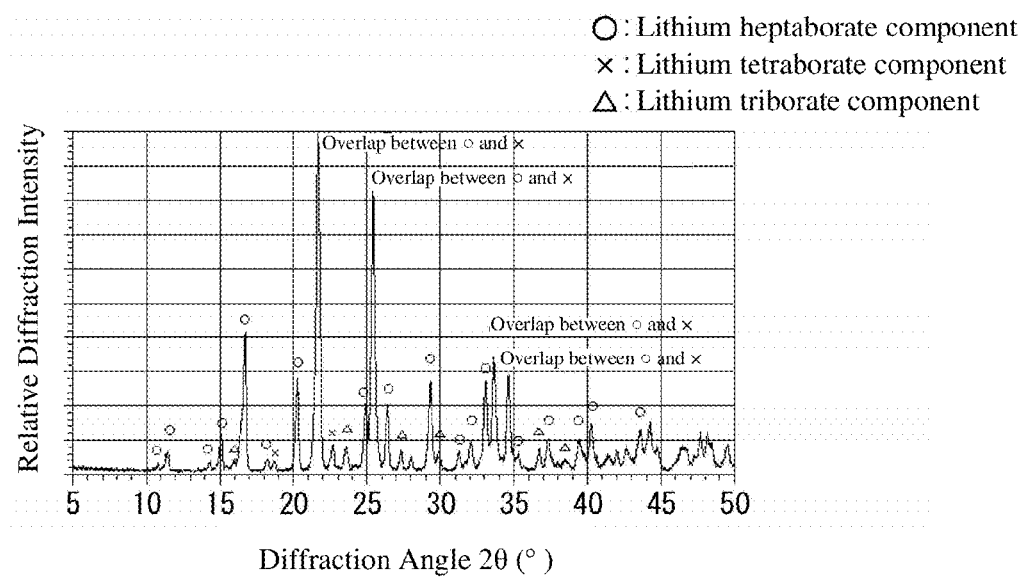
FIG. 8 is presented to identify the components of a thermoluminescent phosphor according to the first embodiment.
Figure 9:
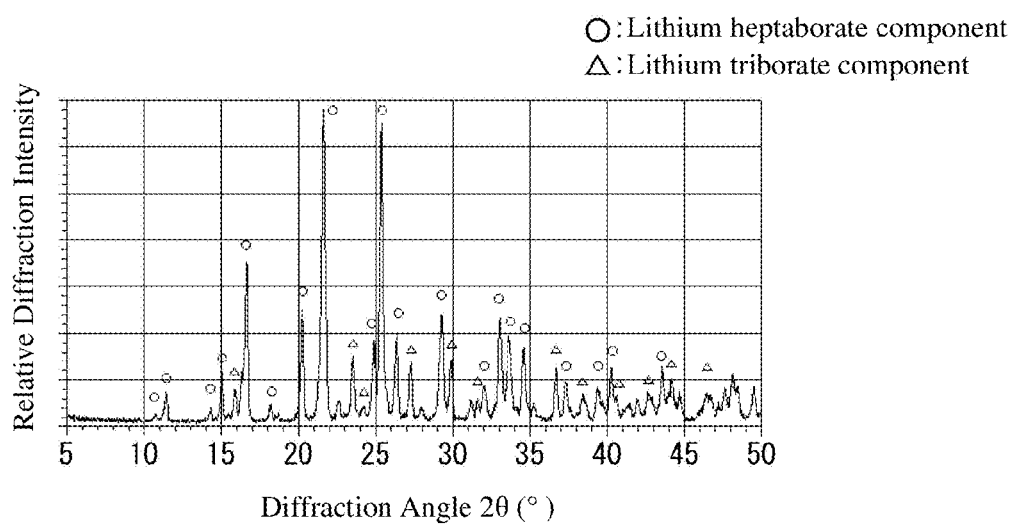
FIG. 9 is presented to identify the components of a thermoluminescent phosphor according to the first embodiment.
Figure 10:
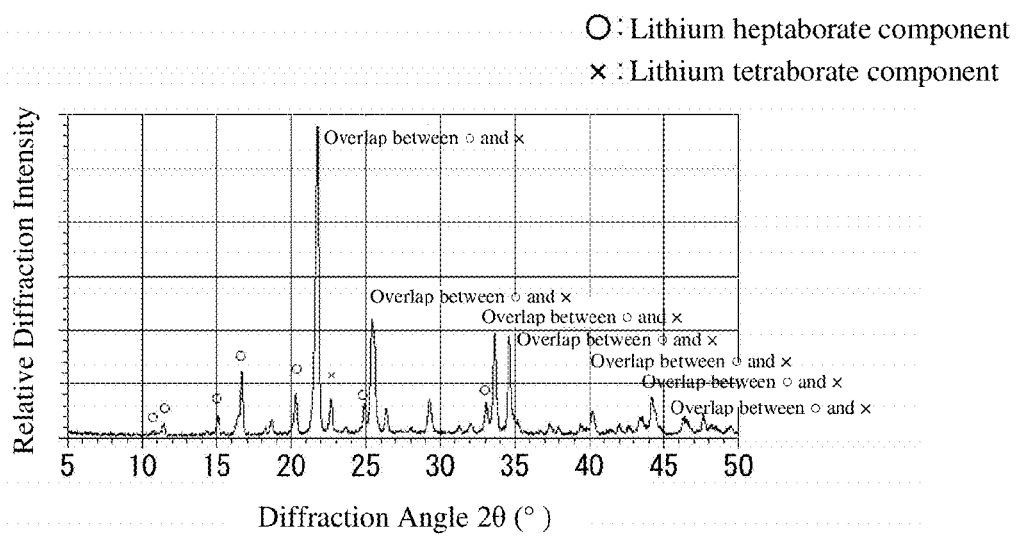
FIG. 10 is presented to identify the components of a thermoluminescent phosphor according to the first embodiment.
Figure 11:
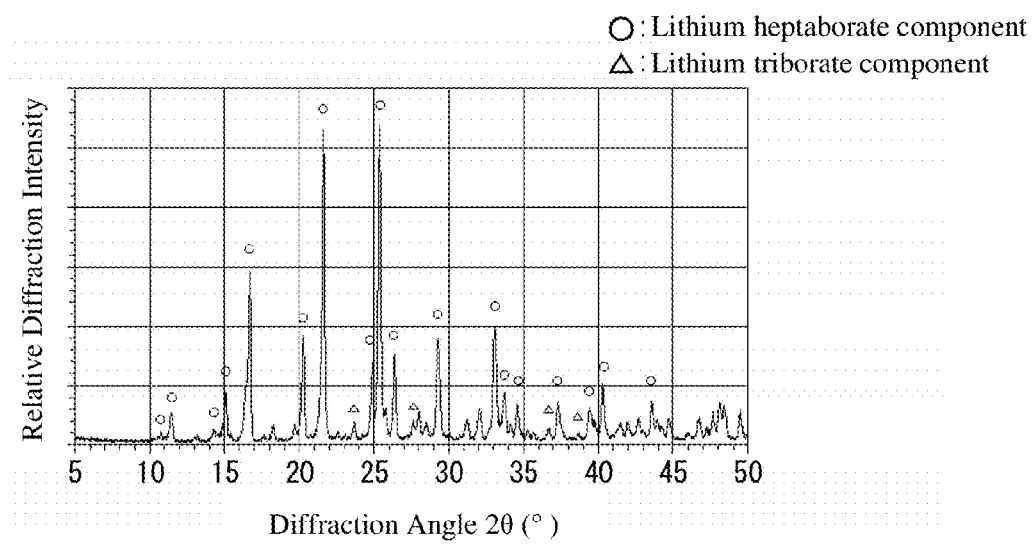
FIG. 11 is presented to identify the components of a thermoluminescent phosphor according to the first embodiment.

FIG. 7 shows an XRD spectrum of Sample c2, FIG. 8 shows an XRD spectrum of Sample c3, FIG. 9 shows an XRD spectrum of Sample c4, FIG. 10 shows an XRD spectrum of Sample d2, and FIG. 11 shows an XRD spectrum of Sample d4. Each of these figures shows the relative diffraction intensity on the vertical axis and the diffraction angle (unit: °) on the horizontal axis.

As for the XRD spectra shown in FIGS. 7, 8, 9, 10, and 11, the peaks are marked with ○ (circle) for lithium heptaborate, x (cross mark) for lithium tetraborate, and Δ (triangle) for lithium triborate, based on the XRD spectrum of the lithium heptaborate shown in FIG. 3(B), the XRD spectrum of the lithium tetraborate shown in FIG. 4(B), and the XRD spectrum of the lithium triborate shown in FIG. 6(B), which are described above.

FIGS. 7, 8, 9, 10, and 11 show that, in all of the XRD spectra of Samples c2, c3, c4, d2, and d4, lithium heptaborate exhibited peaks with high diffraction intensities, compared with the peaks exhibited by lithium tetraborate and lithium triborate.

Thus, it was confirmed that Samples c2, c3, c4, d2, and d4 were theremoluminescent phosphors consisting chiefly of lithium heptaborate whose content was the highest and further containing either one or both of lithium tetraborate and lithium triborate.

In Sample c3 shown in FIG. 8, Sample d2 shown in FIG. 10, and Sample d4 shown in FIG. 11, in particular, lithium heptaborate exhibited peaks with high diffraction intensities, compared with lithium tetraborate and lithium triborate. From this point, it was found that the contents of lithium heptaborate constituting the thermoluminescent phosphors were high.

The results shown in FIGS. 3(A) and 3(B), 4(A) and 4(B), 5(A) and 5(B), 6(A) and 6(B), and 7, 8, 9, 10, and 11 confirmed that, in the first embodiment, a thermoluminescent phosphor comprising lithium heptaborate as a component can be produced under the conditions of the production of Samples c2, c3, c4, d2, d3, and d4, more specifically, by mixing lithium tetraborate and boron oxide in the molar ratio of 3:1, 6:1, or 2:1 in the first step and subjecting the resulting mixture to thermal treatment at a temperature within the range of from 800° C. to 850° C. in the second step.

Further, the yield of lithium heptaborate was increased in Samples c3, d2, d3, and d4, in particular, Sample d3, and this result confirmed that, in the first embodiment, the yield of lithium heptaborate can be increased by mixing lithium tetraborate and boron oxide in the molar ratio of 3:1 in the first step and subjecting the resulting mixture to thermal treatment at the temperature of 850° C. in the second step.

Moreover, as already described, the thermoluminescent phosphor Samples c2, c3, c4, d2, d3, and d4, in particular, Sample d3, exhibited high emission intensities of thermoluminescence (see FIGS. 2(A) and 2(B)). This result confirmed that, by adjusting to be a high value the content of lithium heptaborate as a component of a thermoluminescent phosphor, the emission intensity of thermoluminescence of the thermoluminescent phosphor can be increased as compared with the case of a thermoluminescent phosphor whose lithium tetraborate or lithium triborate content is high.

In particular, when comparing the emission intensities of Samples a1 and e2 consisting chiefly of lithium tetraborate or Sample b5 consisting chiefly of lithium triborate with the emission intensity of Sample d3 consisting chiefly of lithium heptaborate, it is clear from FIGS. 2(A) and 2(B) described above that Sample d3 exhibited high emission intensity.

Thus, it is advantageous to use lithium heptaborate as a base material to constitute a thermoluminescent phosphor, as compared with the case of using lithium tetraborate or lithium triborate as a base material.

The present inventors conducted another experiment to determine a preferred amount of copper(II) oxide to be added as a material when forming a mixture in the first step described above.

Figure 12:
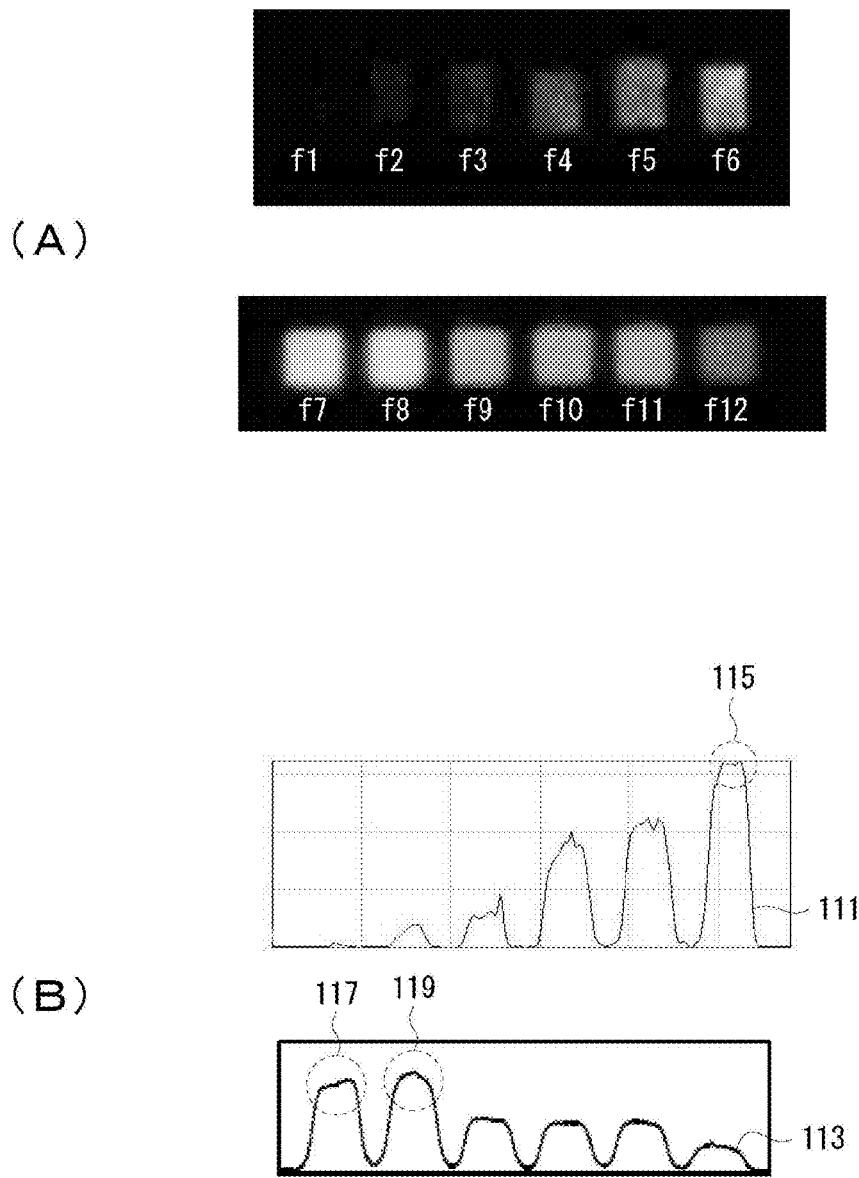
FIGS. 12(A) and 12(B) are presented to compare the emission intensities of thermoluminescence of thermoluminescent phosphors according to the first embodiment.

This experiment is described below with reference to FIG. 12.

In this experiment, a plurality of thermoluminescent phosphors were prepared as samples by incorporating copper(II) oxide in the first step such that the copper(II) oxide concentrations of mixtures obtained were different from one another.

More specifically, in the case of Sample f1, no copper(II) oxide was added to form a mixture in the first step. In the case of Sample f2, copper(II) oxide was added to form a mixture having the copper(II) oxide concentration of 0.01 wt %. In the case of Sample f3, copper(II) oxide was added to form a mixture having the copper(II) oxide concentration of 0.03 wt %. In the case of Sample f4, copper(II) oxide was added to form a mixture having the copper(II) oxide concentration of 0.05 wt %. In the case of Sample f5, copper(II) oxide was added to form a mixture having the copper(II) oxide concentration of 0.07 wt %. In the case of Sample f6, copper(II) oxide was added to form a mixture having the copper(II) oxide concentration of 0.10 wt %. In the case of Sample f7, copper(II) oxide was added to form a mixture having the copper(II) oxide concentration of 0.10 wt %, which was the same as in Sample f6. In the case of Sample f8, copper(II) oxide was added to form a mixture having the copper(II) oxide concentration of 0.35 wt %. In the case of Sample f9, copper(II) oxide was added to form a mixture having the copper(II) oxide concentration of 0.70 wt %. In the case of Sample f10, copper(II) oxide was added to form a mixture having the copper(II) oxide concentration of 1.00 wt %. In the case of Sample f11, copper(II) oxide was added to form a mixture having the copper(II) oxide concentration of 2.00 wt %. In the case of Sample f12, copper(II) oxide was added to form a mixture having the copper(II) oxide concentration of 5.00 wt %.

Each of these samples was prepared by mixing lithium tetraborate and boron oxide in the molar ratio of 3:1 in the first step and subjecting the resulting mixture to thermal treatment at 850° C. in the second step.

Each of these samples was irradiated with 1 Gy of X rays using an irradiator apparatus with an X-ray tube voltage of 6 MV. Subsequently, the each sample was housed in a dark box and exposure with a CCD camera was started, and the samples were heated to 135° C. in 20 seconds and their emission intensities were observed for 280 seconds while maintaining them at the temperature of 135° C.

It is to be noted that, in this experiment, Samples f1 to f6 were aligned on one metal plate and the foregoing irradiation with X rays, heating, and observation of the thermoluminescence were performed on the respective samples at the same time. Likewise, Samples f7 to f12 were aligned on one metal plate and irradiation with X rays, heating, and observation of the thermoluminescence were performed on the respective samples at the same time.

FIGS. 12(A) and 12(B) show the results of this experiment.

FIG. 12(A) is captured images of light emission caused by thermoluminescence of the respective samples described above. It is to be noted that a cooled CCD camera (ATK-314L produced by ATIK Instruments) was used to capture these images.

It is also to be noted that the light emissions marked with symbols f1 to f12 shown in FIG. 12(A) correspond respectively to the light emissions from Samples f1 to f12 described above. That is, the alignment of the samples, which were aligned on the metal plate when conducting this experiment, corresponds to the alignment of the symbols shown in FIG. 12(A).

FIG. 12(B) is presented to compare the emission intensities of thermoluminescence of the samples, and the vertical axis shows the relative emission intensities and the horizontal axis corresponds to the positions of the samples each of which is marked with a symbol in FIG. 12(A). More specifically, the intensity distribution line 111 shown in the upper figure in FIG. 12(B) indicates the emission intensity distribution of Samples f1 to f6 and the intensity distribution line 113 shown in the lower figure in FIG. 12(B) indicates the emission intensity distribution of Samples f7 to f12. It is to be noted that these emission intensities were determined by capturing an image of the thermoluminescence with the cooled CCD camera described above (ATK-314L produced by ATIK Instruments) and then analyzing the image with ImageJ (registered trademark), which is a well-known image-processing software.

It is to be noted that Samples f6 and f7 were prepared under identical conditions in both the first and second steps, as already described. Hence, peak 115 indicating the emission intensity of Sample f6 and peak 117 indicating the emission intensity of Sample f7 are substantially the same in emission intensity.

The results shown in FIG. 12(A) can clearly confirm that Samples f6, f7, and f8 emitted high-intensity light, compared with the other samples.

Further, as is clear from each intensity distribution line shown in FIG. 12(B), peak 115 indicating the emission intensity of Sample f6, peak 117 indicating the emission intensity of Sample f7, and peak 119 indicating the emission intensity of Sample f8 exhibit high emission intensities, compared with those of the other samples. This result confirmed that, in the first embodiment, the emission intensity of thermoluminescence of a thermoluminescent phosphor to be produced can be increased by adding copper(II) oxide in the first step such that the copper(II) oxide concentration of a mixture obtained is within the range of from 0.10 wt % to 0.35 wt %.

Next, the present inventors conducted an experiment to determine the temperature properties and wavelength characteristics of a thermoluminescent phosphor to be produced in the first embodiment.

This experiment is described below with reference to FIGS. 13 and 14.

A sample used in this experiment is a thermoluminescent phosphor prepared by mixing lithium tetraborate, boron oxide, and copper(II) oxide in the first step so that the lithium tetraborate to boron oxide molar ratio is 3:1 and the copper(II) oxide concentration is 0.35 wt % in the mixture obtained, and then subjecting the mixture to thermal treatment at 850° C. in the second step. To determine the emission intensity of thermoluminescence versus temperature, the thermoluminescent phosphor was irradiated with 20 Gy of X rays using a RINT 2000 X-ray analyzer produced by RIGAKU Corp., and then the emission intensity of thermoluminescence was measured while the thermoluminescent phosphor was being heated at 0.5° C./sec. Further, to determine the emission wavelength of thermoluminescence, the thermoluminescent phosphor was irradiated with 20 Gy of X rays using a SZX-type X-ray analyzer produced by RIGAKU Corp., and then the emission wavelength of thermoluminescence was measured with a PMA-11 multichannel detector produced by Hamamatsu Photonics while the thermoluminescent phosphor was being heated at 1° C./sec.

Figure 13:
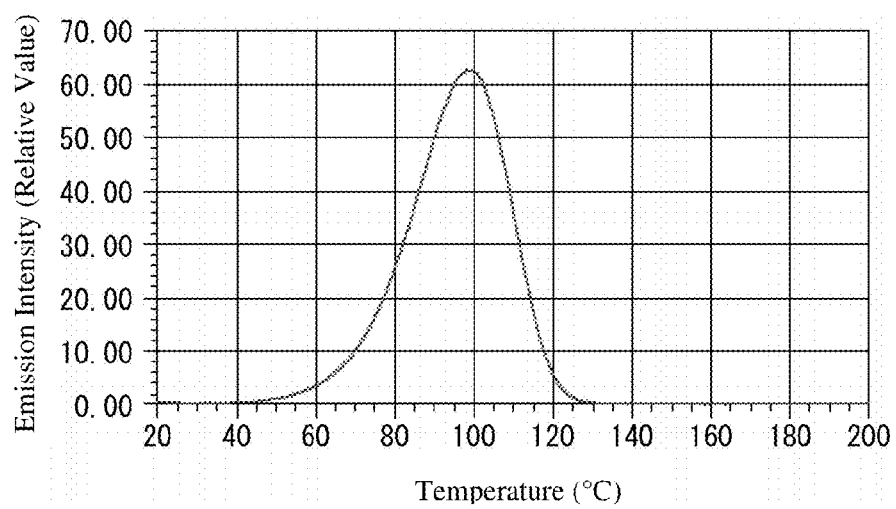
FIG. 13 shows the temperature properties of a thermoluminescent phosphor according to the first embodiment.
Figure 14:
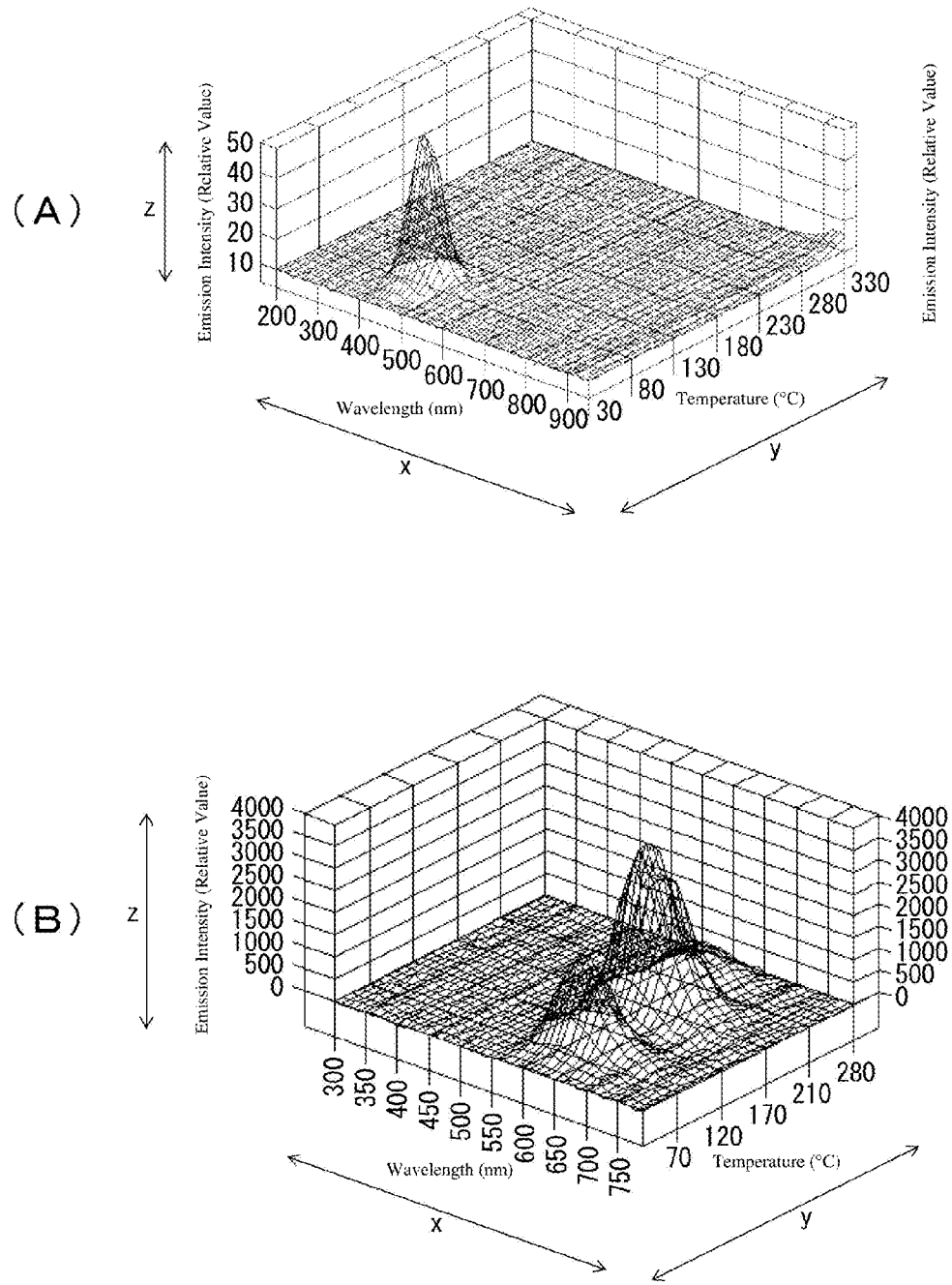
FIGS. 14(A) and 14(B) are presented to compare the wavelength characteristics and temperature properties of a thermoluminescent phosphor according to the first embodiment and those of a thermoluminescent phosphor produced by a conventional technique.

FIG. 13 shows the result of this experiment, showing the temperature properties of the thermoluminescent phosphor to be produced in the first embodiment. The figure shows the relative emission intensity on the vertical axis and the temperature of the thermoluminescent phosphor (unit: ° C.) on the horizontal axis.

FIGS. 14(A) and 14(B) show the results of this experiment and are presented to compare the wavelength characteristics and temperature properties of the thermoluminescent phosphor to be produced in the first embodiment with those of a thermoluminescent phosphor produced by a conventional technique, more specifically, the thermoluminescent phosphor comprising the manganese-containing lithium tetraborate disclosed in Patent Document 1, which is described above. FIG. 14(A) shows the wavelength characteristics and temperature properties of the thermoluminescent phosphor according to the first embodiment and FIG. 14(B) shows the wavelength characteristics and temperature properties of the thermoluminescent phosphor disclosed in Patent Document 1. FIGS. 14(A) and 14(B) each show the thermoluminescence wavelength (unit: nm) on the x-axis and the temperature of the thermoluminescent phosphor (unit: ° C.) on the y-axis. The figures each show the relative emission intensity on the z-axis.

It is to be noted that aluminum (III) was added to the manganese-containing lithium tetraborate shown in FIG. 14(B) in order to increase the emission intensity, as disclosed in Patent Document 1.

As is clear from FIGS. 13 and 14(A), it was confirmed that the emission intensity of thermoluminescence of the thermoluminescent phosphor according to the first embodiment is characterized in that a monomodal emission intensity distribution is present within the temperature range of from 45° C. to 130° C. and that one peak is present at about 98° C. It is to be noted that these measurements were performed with a PMA-11 multichannel detector produced by Hamamatsu Photonics.

The temperature range of from 45° C. to 130° C., in which this distribution of the emission intensity of thermoluminescence is present, includes temperatures at which the foregoing epoxy resin that is preferred as a binder and which is equivalent in effective atomic number to the human body, more specifically, for example, GM-9005 produced by Blenny Giken Corporation, can resist heat optically, that is, it does not discolor.

Hence, to prepare a dosimeter for measuring three-dimensional dose distribution, the thermoluminescent phosphor according to the first embodiment can form a plate using GM-9005 as a binder. Thus, the thermoluminescent phosphor according to the first embodiment is usable as a material that is used for a dosimeter for measuring three-dimensional dose distribution and which is tissue equivalent to the human body.

Further, in the case of the thermoluminescent phosphor according to the first embodiment, the distribution of the emission intensity of thermoluminescence is a sole and monomodal distribution.

Thus, the relation between the exposure dose and the emission intensity of thermoluminescence is simple, and as a result, complex corrections are not required to be made when calculating the exposure dose from measured emission intensity of thermoluminescence. The details on this point will be described later with reference to FIG. 15.

As for the emission intensity of thermoluminescence of the thermoluminescent phosphor according to the first embodiment, it was also confirmed from FIG. 14(A) that the distribution of the emission intensity of thermoluminescence versus thermoluminescence wavelength is present in the range that is a visible range and a range of wavelengths shorter than 600 nm, more specifically, in the wavelength range of from 400 nm to 550 nm.

In contrast, in the case of the thermoluminescent phosphor disclosed in Patent Document 1, it was confirmed from FIG. 14(B) that the distribution of the emission intensity of thermoluminescence is present in the wavelength range of from 550 nm to 750 nm.

As already described in the section of Background Art, a shorter wavelength envelope of the emission is present in a wavelength range close to 600 nm in the intensity distribution of the heating-caused light emission of manganese-containing lithium tetraborate itself. Hence, if the temperature of the thermoluminescent phosphor disclosed in Patent Document 1 is increased to a temperature at which heating-caused light emission occurs, it is necessary to separate thermoluminescence emission and heating-caused light emission, by using, for example, a near-infrared cut filter.

In contrast, in the case of the thermoluminescent phosphor according to the first embodiment, the distribution of the emission intensity of thermoluminescence is present in a range of wavelengths shorter than 600 nm, and thus, it is not necessary to consider the heating-caused light emission described above and it is thus not necessary to use, for example, a near-infrared cut filter.

Further, as for the thermoluminescence of the thermoluminescent phosphor according to the first embodiment, the distribution of the emission intensity of thermoluminescence is present in a wavelength range within a visible range. Hence, even if, for example, an epoxy resin is used as a binder to form a plate, the thermoluminescence is not absorbed by the resin, and thus, the emission intensity of thermoluminescence is not decreased.

Next, the present inventors conducted an experiment to determine the relation between the emission intensity of thermoluminescence of the thermoluminescent phosphor to be produced in the first embodiment and the exposure dose.

In this experiment, the same thermoluminescent phosphor as that shown in FIGS. 13 and 14(A) described above was irradiated with different doses of X rays (0.25 Gy, 0.5 Gy, 1 Gy, 2 Gy) using an irradiator apparatus with an X-ray tube voltage of 6 MV, and then the emission intensity of thermoluminescence versus each exposure dose was observed. It is to be noted that the X-ray irradiated thermoluminescent phosphor was heated to 135° C. at 0.5° C./sec in a dark box before observing the emission intensity.

Figure 15:
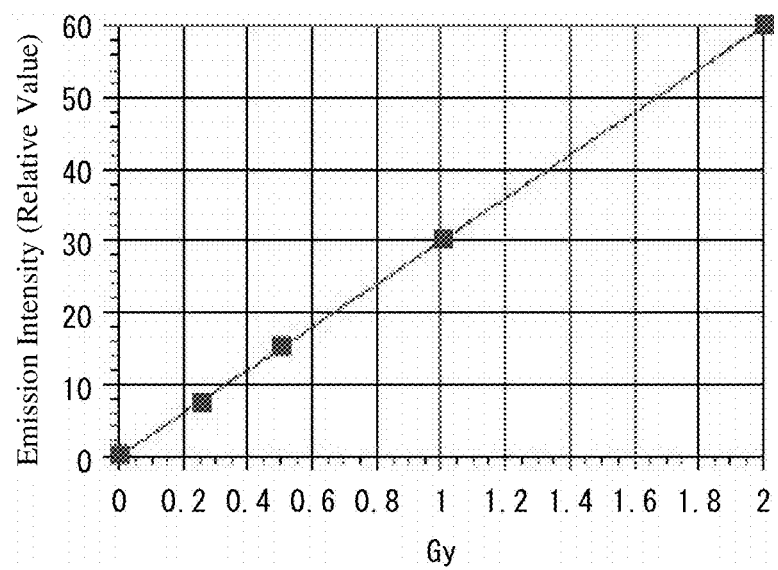
FIG. 15 shows the relation between the emission intensity of thermoluminescence and the exposure dose, in a thermoluminescent phosphor according to the first embodiment.

FIG. 15 shows the result of this experiment, showing the relation between the emission intensity of thermoluminescence of the thermoluminescent phosphor to be produced in the first embodiment and the exposure dose. FIG. 15 shows the relative emission intensity on the vertical axis and the X-ray radiation dose, that is, the exposure dose applied to the thermoluminescent phosphor (unit: Gy), on the horizontal axis. It is to be noted that, in this experiment, a SYNERGY linac produced by Elekta was used as an X-ray irradiator apparatus and a cooled CCD camera (ATK-314L produced by ATIK Instruments) was used for the measurement of the emission intensity.

It can be confirmed from FIG. 15 that the emission intensity of thermoluminescence of the thermoluminescent phosphor according to the first embodiment increases linearly with the increase in the exposure dose, given that the thermoluminescent phosphor had the relative value 7 at the exposure dose of 0.25 Gy, the relative value 15 at the exposure dose of 0.50 Gy, the relative value 30 at the exposure dose of 1.0 Gy, and the relative value 60 at the exposure dose of 2.0 Gy.

Thus, this result confirmed that a dosimeter using as a material a thermoluminescent phosphor according to the first embodiment can calculate the exposure dose from measured emission intensity of thermoluminescence without making complex corrections.

The invention claimed is:

1. A thermoluminescent phosphor comprising lithium heptaborate as a base material and copper as a luminescent center present in the base material, wherein the distribution of the emission intensity of thermoluminescence versus wavelength is a sole and monomodal distribution and present in a visible range of wavelengths shorter than 600 nm.

2. The thermoluminescent phosphor of claim 1, wherein the distribution of the emission intensity versus wavelength is present in a wavelength range of from 400 nm to 550 nm.

3. The thermoluminescent phosphor of claim 1, wherein the distribution of the emission intensity of thermoluminescence versus temperature is a sole and monomodal distribution in the range of from 45° C. to 130° C.

4. A method of producing a thermoluminescent phosphor comprising lithium heptaborate as a base material and copper as a luminescent center present in the base material, the method comprising:
   a first step for mixing lithium tetraborate, boron oxide, and copper(II) oxide together to form a mixture,
   a second step for subjecting the mixture to thermal treatment to change the mixture into the thermoluminescent phosphor comprising lithium heptaborate as a base material and copper as a luminescent center present in the base material,
   wherein the lithium tetraborate and the boron oxide are mixed in the molar ratio of 3:1 in the first step.

5. A method of producing a thermoluminescent phosphor comprising lithium heptaborate as a base material and copper as a luminescent center present in the base material, the method comprising:
   a first step for mixing lithium tetraborate, boron oxide, and copper(II) oxide together to form a mixture,
   a second step for subjecting the mixture to thermal treatment to change the mixture into the thermoluminescent phosphor comprising lithium heptaborate as a base material and copper as a luminescent center present in the base material,
   wherein the lithium tetraborate and the boron oxide are mixed in the molar ratio of 6:1 in the first step.

6. A method of producing a thermoluminescent phosphor comprising lithium heptaborate as a base material and copper as a luminescent center present in the base material, the method comprising:
   a first step for mixing lithium tetraborate, boron oxide, and copper(II) oxide together to form a mixture,
   a second step for subjecting the mixture to thermal treatment to change the mixture into the thermoluminescent phosphor comprising lithium heptaborate as a base material and copper as a luminescent center present in the base material,
   wherein the lithium tetraborate and the boron oxide are mixed in the molar ratio of 2:1 in the first step.

7. The method of producing the thermoluminescent phosphor of claim 4, wherein the thermal treatment is performed at a temperature within the range of from 800° C. to 850° C. in the second step.

8. The method of producing the thermoluminescent phosphor of claim 7, wherein the thermal treatment is performed at the temperature of 850° C. in the second step.

9. The method of producing the thermoluminescent phosphor of claim 4, wherein the copper(II) oxide is incorporated in the first step in a copper(II) oxide concentration within the range of from 0.1 wt % to 0.35 wt % in the mixture.

10. The method of producing the thermoluminescent phosphor of claim 4, wherein the weights of the lithium tetraborate, the boron oxide, and the copper(II) oxide are adjusted and mixed together in the first step to thereby adjust the effective atomic number of the thermoluminescent phosphor.

* * * * *